US010667938B2

(12) United States Patent
Bonutti et al.

(10) Patent No.: US 10,667,938 B2
(45) Date of Patent: Jun. 2, 2020

(54) ORTHOSIS FOR RANGE OF MOTION

(71) Applicant: BONUTTI RESEARCH, INC., Effingham, IL (US)

(72) Inventors: Boris Bonutti, Effingham, IL (US); Glen A. Phillips, Effingham, IL (US); Peter M. Bonutti, Manalapan, FL (US)

(73) Assignee: Bonutti Research, Inc., Effingham, IL (US)

( * ) Notice: Subject to any disclaimer, the term of this patent is extended or adjusted under 35 U.S.C. 154(b) by 710 days.

(21) Appl. No.: 15/287,150

(22) Filed: Oct. 6, 2016

(65) Prior Publication Data
US 2017/0100295 A1 Apr. 13, 2017

Related U.S. Application Data

(60) Provisional application No. 62/238,690, filed on Oct. 7, 2015.

(51) Int. Cl.
*A61F 5/01* (2006.01)
*A61H 1/00* (2006.01)
*A61H 5/00* (2006.01)
*A61H 1/02* (2006.01)

(52) U.S. Cl.
CPC ............ *A61F 5/013* (2013.01); *A61H 1/0274* (2013.01); *A61F 2005/0155* (2013.01); *A61H 2001/0203* (2013.01); *A61H 2201/1207* (2013.01); *A61H 2201/1253* (2013.01); *A61H 2201/1276* (2013.01); *A61H 2201/165* (2013.01); *A61H 2201/1635* (2013.01)

(58) Field of Classification Search
CPC .. A61H 1/0274; A61H 1/0281; A61H 1/0277; A61H 1/0237; A61H 1/02; A61H 2201/1669; A63B 21/4047; A63B 23/03508
USPC .......................................... 601/23
See application file for complete search history.

(56) References Cited

U.S. PATENT DOCUMENTS

| 4,612,919 A | * | 9/1986 | Best | ......................... A61F 5/373 602/16 |
| 4,724,827 A | * | 2/1988 | Schenck | .............. A61H 1/0288 601/40 |
| 5,052,379 A | * | 10/1991 | Airy | ...................... A61F 5/0125 482/112 |
| 5,376,091 A | * | 12/1994 | Hotchkiss | .............. A61B 17/62 602/22 |
| 7,449,023 B2 | * | 11/2008 | Walulik | .............. A61B 17/6416 606/59 |

(Continued)

Primary Examiner — Justine R Yu
Assistant Examiner — Alexander Morales
(74) Attorney, Agent, or Firm — Stinson LLP

(57) ABSTRACT

An orthosis for increasing range of motion of a body joint. The orthosis includes a rotational linkage mechanism having a driving link and a driven link configured for rotation about a joint axis. The driven link is selectively attachable to a body part to rotate the body part about the joint axis. A dynamic force mechanism is operatively connected between the driving link and driven link to impart a dynamic force upon the driven link when the driving link rotates relative to the driven link and the driven link resists rotation with the driving link due to a resistance force imparted on the driven link by the body part reaching a maximum range of motion. The dynamic force is transferred through the driven link to the body part.

19 Claims, 14 Drawing Sheets

(56) References Cited

U.S. PATENT DOCUMENTS

| | | | |
|---|---|---|---|
| 8,251,935 B2* | 8/2012 | Bonutti | A61F 5/0127 602/23 |
| 2003/0144614 A1* | 7/2003 | Cordo | A61H 1/02 601/27 |
| 2004/0082885 A1* | 4/2004 | Culhane | A61H 1/0277 601/5 |
| 2004/0243025 A1* | 12/2004 | Peles | A61H 1/0277 601/5 |
| 2009/0326422 A1* | 12/2009 | Hoffman | A61F 5/013 601/5 |

* cited by examiner

ORTHOSIS FOR RANGE OF MOTION

CROSS-REFERENCE TO RELATED APPLICATIONS

The present application claims the benefit of U.S. Provisional Application Ser. No. 62/238,690, filed Oct. 7, 2015, the entirety of which is hereby incorporated by reference.

FIELD

The present disclosure generally relates to an orthosis for treating a joint of a subject, and in particular, an orthosis for increasing range of motion of the joint of the subject.

BACKGROUND

In a joint of a body, its range of motion depends upon the anatomy and condition of that joint and on the particular genetics of each individual. Many joints primarily move either in flexion or extension, although some joints also are capable of rotational movement in varying degrees. Flexion is to bend the joint and extension is to straighten the joint; however, in the orthopedic convention some joints only flex. Some joints, such as the knee, may exhibit a slight internal or external rotation during flexion or extension. Other joints, such as the elbow or shoulder, not only flex and extend but also exhibit more rotational range of motion, which allows them to move in multiple planes. The elbow joint, for instance, is capable of supination and pronation, which is rotation of the hand about the longitudinal axis of the forearm placing the palm up or the palm down. Likewise, the shoulder is capable of a combination of movements, such as abduction, internal rotation, external rotation, flexion and extension.

When a joint is injured, either by trauma or by surgery, scar tissue can form or tissue can contract and consequently limit the range of motion of the joint. For example, adhesions can form between tissues and the muscle can contract itself with permanent muscle contracture or tissue hypertrophy such as capsular tissue or skin tissue. Lost range of motion may also result from trauma such as excessive temperature (e.g., thermal or chemical burns) or surgical trauma so that tissue planes which normally glide across each other may become adhered together to markedly restrict motion. The adhered tissues may result from chemical bonds, tissue hypertrophy, proteins such as Actin or Myosin in the tissue, or simply from bleeding and immobilization. It is often possible to mediate, and possibly even correct this condition by use of a range-of-motion (ROM) orthosis.

ROM orthoses are used during physical rehabilitative therapy to increase the range-of-motion of a body joint. Additionally, they also may be used for tissue transport, bone lengthening, stretching of skin or other tissue, tissue fascia, and the like. When used to treat a joint, the device typically is attached on body portions on opposite sides of the joint so that it can apply a force to move the joint in opposition to the contraction.

A number of different configurations and protocols may be used to increase the range of motion of a joint. For example, stress relaxation techniques may be used to apply variable forces to the joint or tissue while in a constant position. "Stress relaxation" is the reduction of forces, over time, in a material that is stretched and held at a constant length. Relaxation occurs because of the realignment of fibers and elongation of the material when the tissue is held at a fixed position over time. Treatment methods that use stress relaxation are serial casting and static splinting. One example of devices utilizing stress relaxation is the JAS EZ orthosis, Joint Active Systems, Inc., Effingham, Ill.

Sequential application of stress relaxation techniques, also known as Static Progressive Stretch ("SPS") uses the biomechanical principles of stress relaxation to restore range of motion (ROM) in joint contractures. SPS is the incremental application of stress relaxation—stretch to position to allow tissue forces to drop as tissues stretch, and then stretching the tissue further by moving the device to a new position—repeated application of constant displacement with variable force. In an SPS protocol, the patient is fitted with an orthosis about the joint. The orthosis is operated to stretch the joint until there is tissue/muscle resistance. The orthosis maintains the joint in this position for a set time period, for example five minutes, allowing for stress relaxation. The orthosis is then operated to incrementally increase the stretch in the tissue and again held in position for the set time period. The process of incrementally increasing the stretch in the tissue is continued, with the pattern being repeated for a maximum total session time, for example 30 minutes. The protocol can be progressed by increasing the time period, total treatment time, or with the addition of sessions per day. Additionally, the applied force may also be increased.

Another treatment protocol uses principles of creep to constantly apply a force over variable displacement. In other words, techniques and devices utilizing principles of creep involve continued deformation with the application of a fixed load. For tissue, the deformation and elongation are continuous but slow (requiring hours to days to obtain plastic deformation), and the material is kept under a constant state of stress. Treatment methods such as traction therapy and dynamic splinting are based on the properties of creep.

BRIEF DESCRIPTION OF THE DRAWINGS

Corresponding reference characters indicate corresponding parts throughout the drawings.

DETAILED DESCRIPTION

Figure 1:
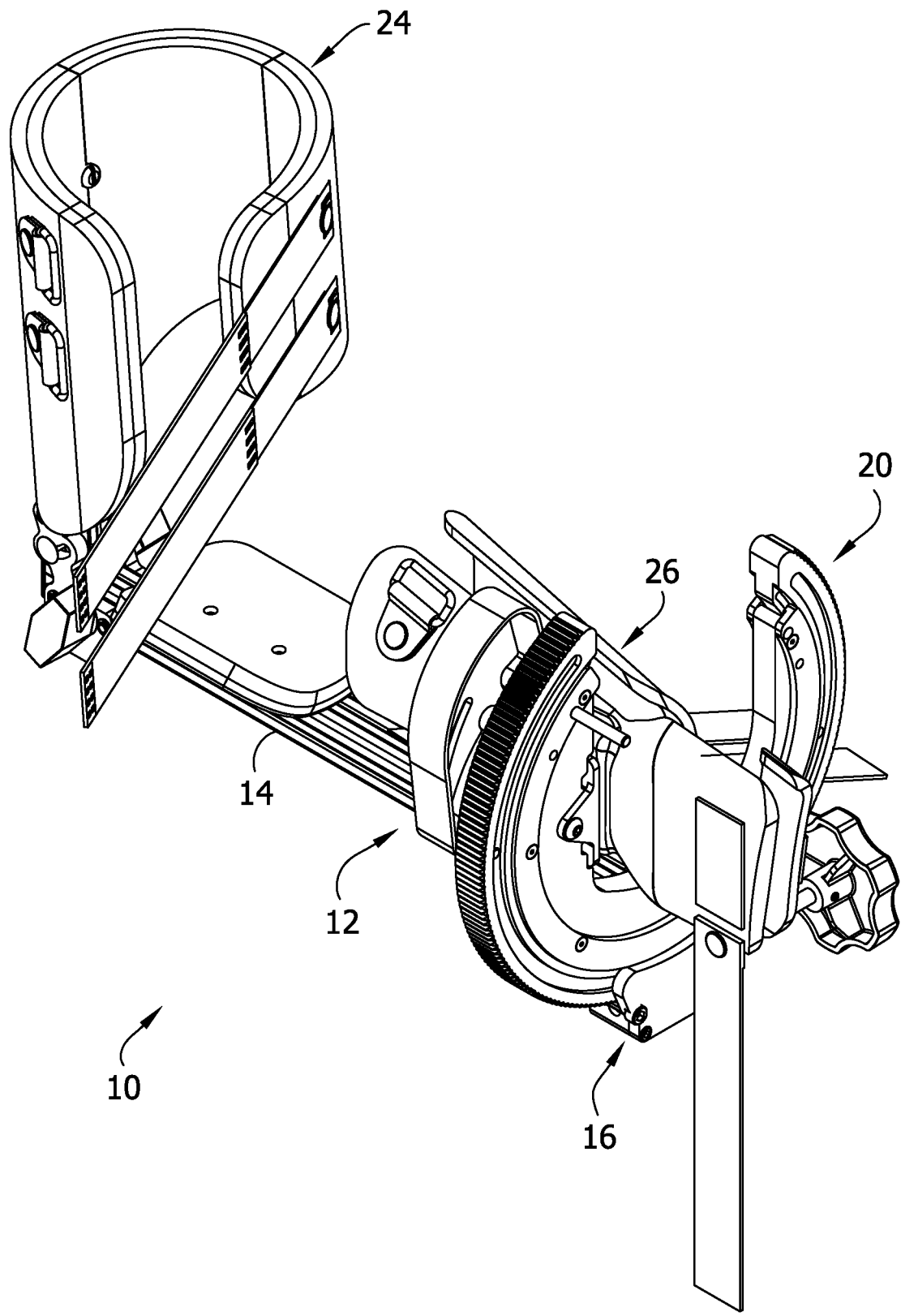
FIG. 1 is a perspective of an orthosis.

Referring to FIG. 1, an orthosis for treating a joint of a subject is generally indicated at reference numeral 10. The general structure of the orthosis 10 is suitable for treating a forearm of the body. In particular, the configuration of the orthosis 10 is suitable for increasing range of motion of the forearm in supination and pronation. Various teachings of the orthosis 10 are also suitable for orthoses for treating other joints, including but not limited to the shoulder joint, radioulnar joint, hinge joints (e.g., knee joint, elbow joint, and ankle joint), or ellipsoidal joints (e.g., wrist joint, finger joints, toe joints). Thus, in other embodiments the teachings of the illustrated orthosis may be suitable for increasing range of motion of a body joint in adduction and/or abduction, pronation and/or supination, inward and/or outward rotation, flexion and/or extension, etc.

The illustrated orthosis 10 is a dynamic stretch orthosis comprising a dynamic force mechanism, generally indicated at 12, for applying a dynamic stretch to a forearm in either supination or pronation. An actuator mechanism, generally indicated at 16, is operatively connected to a rotational linkage mechanism, generally indicated at 20, for transmitting force to the dynamic force mechanism 12, as will be explained in further detail below. A frame 14 mounts first and second cuffs, generally indicated at 24, 26 (broadly, body portion securement members), for coupling body portions to the orthosis 10. In the illustrated embodiment, the first cuff 24 is an upper arm cuff configured to be secured around an upper arm portion of a body. The second cuff 26 is a hand and wrist splint configured to be secured around the hand and wrist of a body so that the hand and wrist are inhibited from rotating relative to the splint.

As will be apparent from this disclosure, when the first and second cuffs 24, 26 are properly secured to an arm, the orthosis 10 can be used to stretch the forearm in pronation or supination. Moreover, the orthosis 10 may be used as a combination dynamic and static-progressive stretch orthosis. It is understood that in other embodiments, the dynamic force mechanisms may be omitted without departing from the scope of the invention, thereby making the orthosis suitable as a static stretch or static progressive stretch orthosis by using the illustrated actuator mechanism and/or the linkage mechanism. In addition, it is understood that that in other embodiments the orthosis may include the illustrated dynamic force mechanism, while omitting the illustrated actuator mechanism and/or linkage mechanism. As explained in further detail below, the illustrated orthosis 10 is configured to rotate the rotational linkage mechanism 20 to rotate a forearm in either pronation or supination until a maximum range of motion of the forearm has been reached; at which point, the orthosis 10 is configured to further rotate a link in the rotational linkage mechanism to impart a dynamic force upon the forearm, which urges further pronation or supination of the forearm, thereby increasing the range of motion of the forearm.

Figure 2:
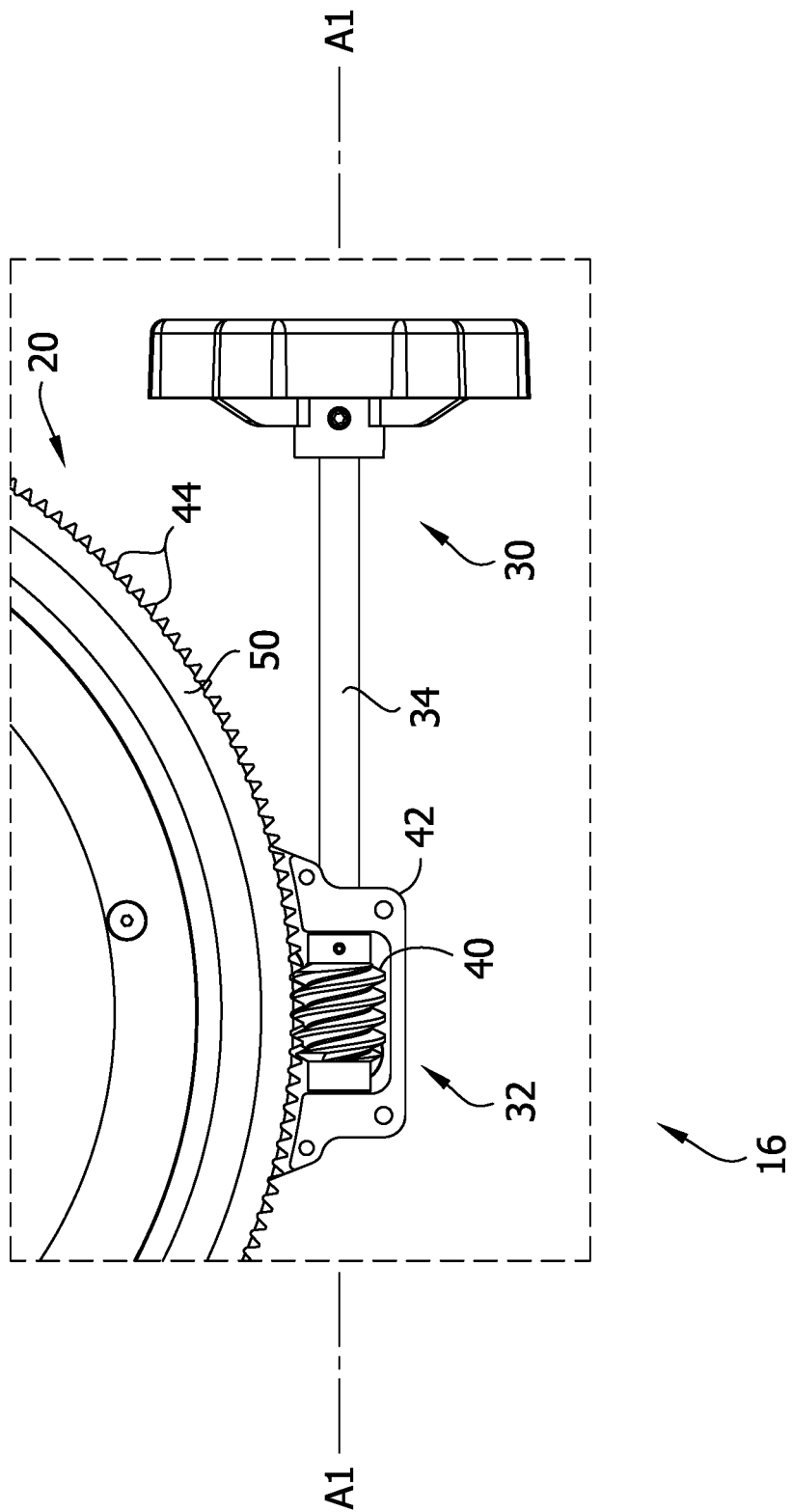
FIG. 2 is an enlarged elevation of a portion of the orthosis with a plate removed to reveal internal components.

Referring to FIG. 2, the actuator mechanism 16 is configured to drive rotation of the rotational linkage mechanism 20. The actuator mechanism 16 includes a drive assembly, generally indicated at 30, and a transmission assembly, generally indicated at 32. In the illustrated embodiment, the drive assembly 30 includes an input shaft 34 operatively connected to the transmission assembly 32 and an actuator knob 36. The knob 36 and input shaft 34 are configured to be conjointly rotated about a drive axis A1 to drive rotation of the transmission assembly 32. The knob 36 is configured to be grasped by a user who rotates the drive assembly 30. But in other embodiments, the input shaft could be operatively connected to a prime mover, such as a motor or engine, for rotating the input shaft.

In the illustrated embodiment, the transmission assembly 32 comprises a worm gear 40 that is received for rotation within a transmission assembly housing 42. The worm gear 40 is operatively connected to the input shaft 34 and is configured to rotate conjointly with the input shaft about the drive axis A1. The worm gear 40 operatively meshes with worm ring teeth 44 of an outer ring member 50 of the rotational linkage mechanism 20 to drive rotation of the rotational linkage mechanism about a joint rotation axis A2 (FIG. 3).

Figure 3:
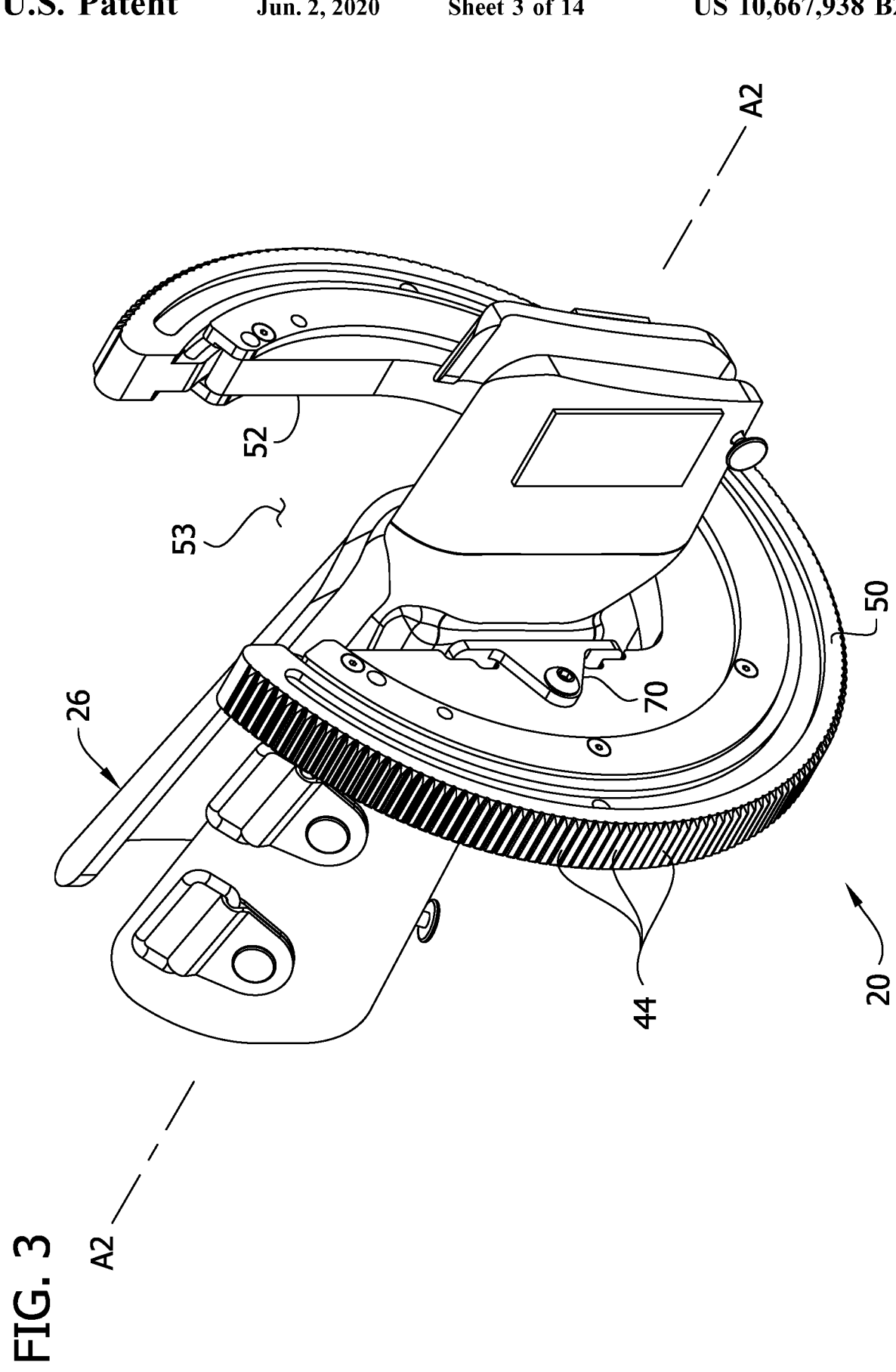
FIG. 3 is a perspective of a rotational linkage mechanism and splint of the orthosis.

Referring to FIG. 3, the rotational linkage mechanism 20 includes the outer ring member 50 and an inner ring member 52. In the illustrated embodiment, each of the ring members 50, 52 is generally circular in shape, but defines a gap 53 for receiving a user's forearm therethrough. The forearm passes through the gap 53 when being installed in the splint 26. In the illustrated rotational linkage mechanism 20, the outer ring member 50 functions generally as a driving link because, as it is driven in rotation about the joint rotation axis A2 by the actuation mechanism 16, it drives rotation of the inner ring member 52. The inner ring member 52 functions generally as a driven link in the rotational linkage mechanism 20 because its rotation about the joint rotation axis A2 is driven by the outer ring member 50. It will be understood that other rotational linkage mechanisms can include driving and driven links that have other configurations without departing from the scope of the invention.

Figure 4A:
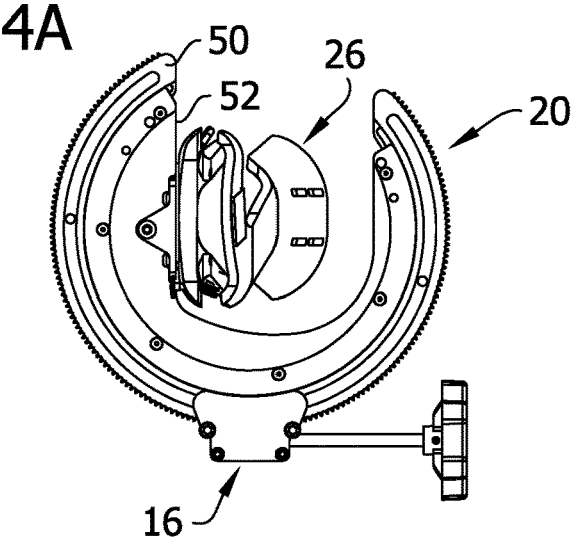
FIGS. 4A-4E are elevations of the rotational linkage mechanism and splint illustrating the rotational linkage mechanism in various configurations.
Figure 4B:
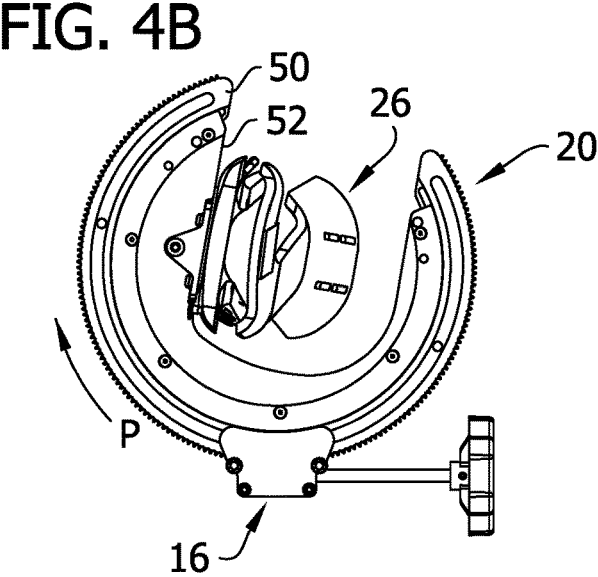
Figure 4D:
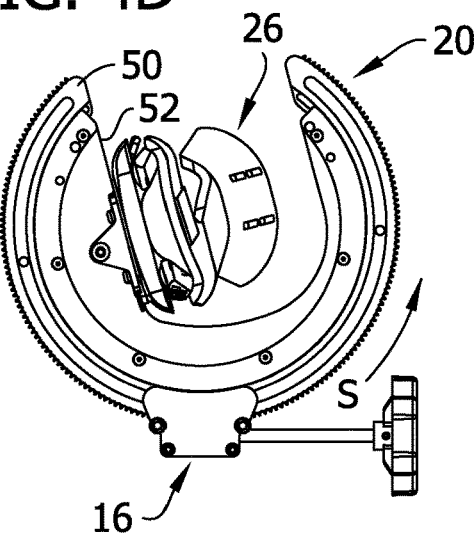
Figure 4C:
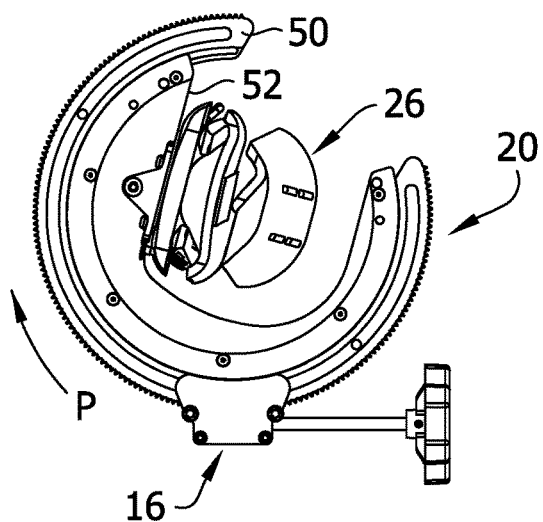

As will be explained in further detail below, the rotational linkage mechanism 20 is configured to operate in a static loading mode and dynamic loading mode. In the static loading mode, the actuation mechanism 16 drives the outer ring member 50 in rotation about the joint rotation axis A2, and the outer ring member, in turn, drives the inner ring member 52 to rotate conjointly therewith. For example, as shown in FIGS. 4A and 4B, the inner and outer ring members 50, 52 can rotate conjointly in a pronation direction P in certain applications of the orthotic 10. Or as shown in FIGS. 4A and 4D, the inner and outer ring members 50, 52 can rotate conjointly in a supination direction S in certain applications of the orthotic 10. In the dynamic loading mode, the actuation mechanism 16 drives the outer ring member 50 to rotate relative to the inner ring member 52 about the joint rotation axis A2. For example, as shown in FIG. 4C, the outer ring member 50 can rotate relative to the inner ring member 52 in the pronation direction P. Or as shown in FIG. 4E, the outer ring member 50 can rotate relative to the inner member 52 in the supination direction S.

Figure 5:
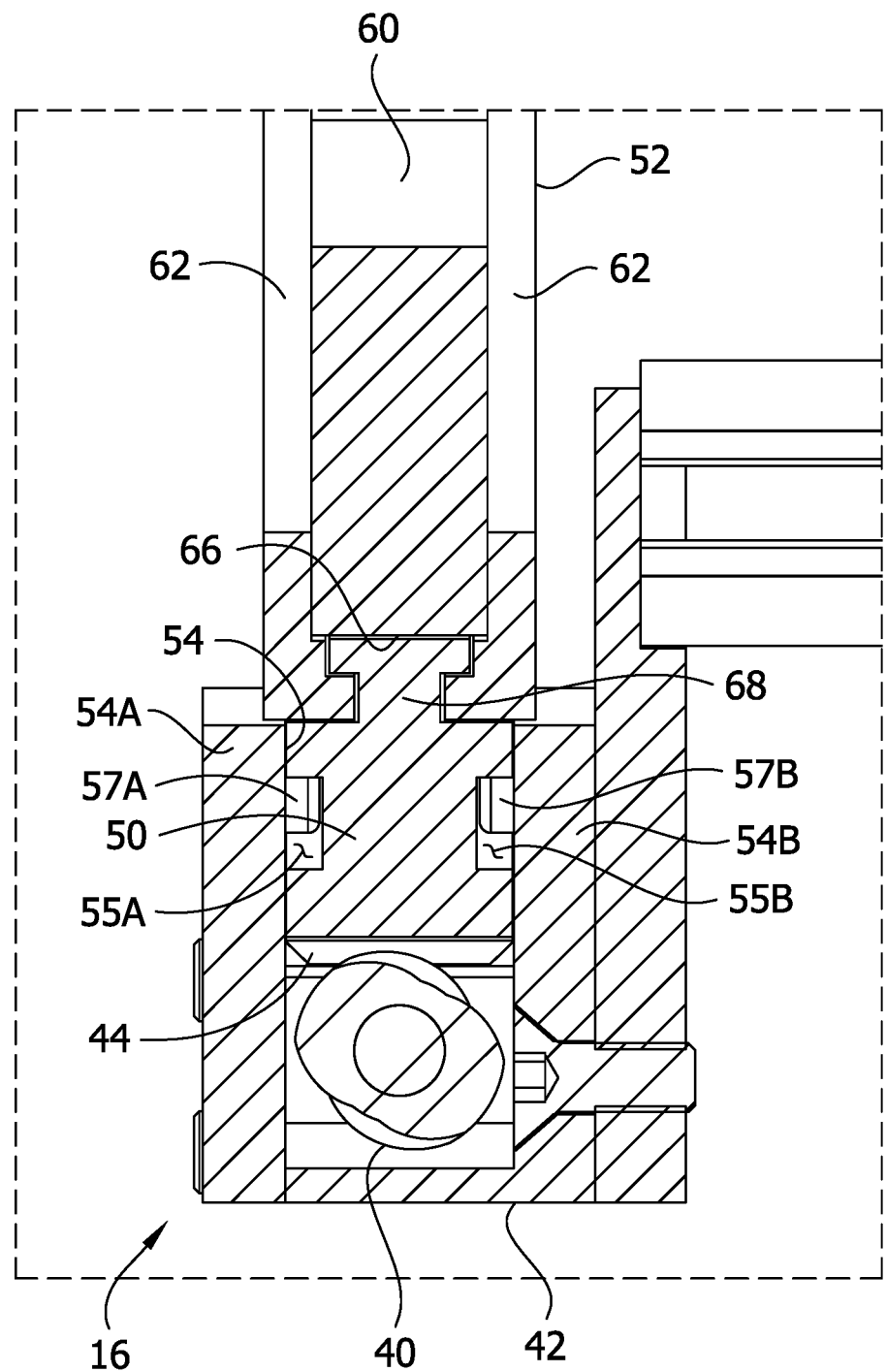
FIG. 5 is an enlarged cross section of the rotational linkage mechanism and an actuation mechanism of the orthosis.

As shown in FIG. 5, the outer ring member 50 is operatively connected to the actuation mechanism 16 for guided rotation about the joint rotation axis A2 in either the static or dynamic loading modes. In the illustrated embodiment, the transmission assembly housing 42 includes a guide 54 for guiding rotation of the rotational linkage mechanism 20 about the joint rotation axis A2. The guide 54 is defined by a distal plate 54A and a proximal plate 54B of the transmission assembly housing 42. The outer ring member 50 is received in a channel between the distal and proximal plates 54A, 54B such that the distal axial surface of the outer ring member slidably engages the distal plate and the proximal axial surface of the outer ring member slidably engages the proximal plate. The distal and proximal axial surfaces of the outer ring member 50 define respective guide channels 55A, 55B. Projections 57A, 57B extend inward from the distal and proximal plates 54A, 54B and are slidingly received in the channels 55A, 55B. As the actuation mechanism 16 rotates the outer ring member 50, the ring member slidably engages the distal and proximal plates 54A, 54B as it rotates through the guide 54. The projections 57A, 57B likewise slide through the channels 55A, 55B to guide rotation of the rotational linkage mechanism about the joint rotation axis A2.

Figure 4E:
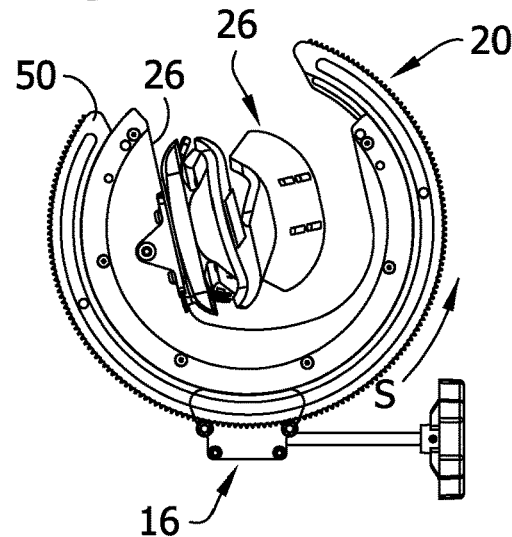
Figure 6:
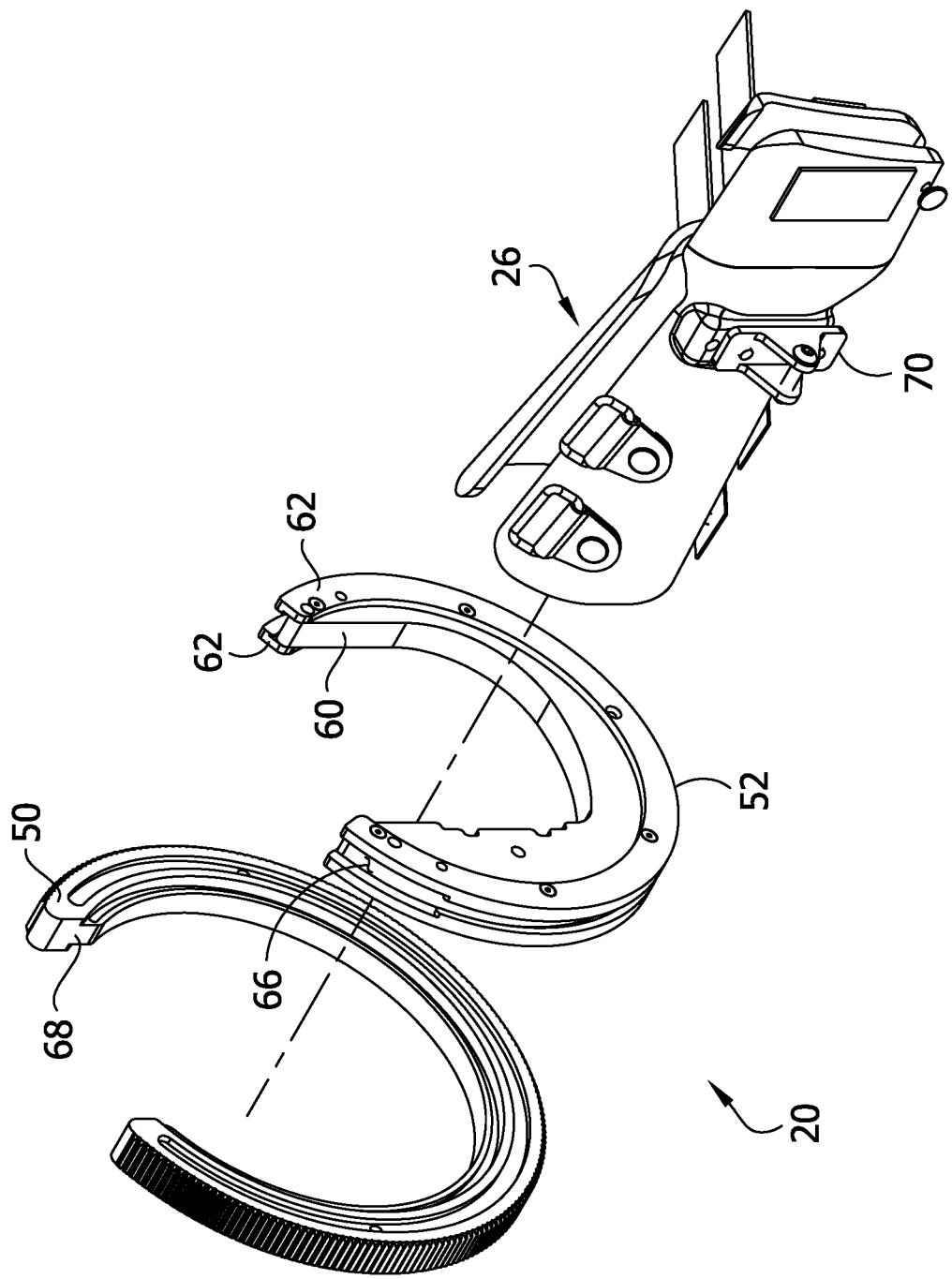
FIG. 6 is an exploded view of the assembly of FIG. 3.

As shown in FIGS. 4C and 4E, the outer ring member 50 is configured to rotate relative to the inner ring member 52 in guided rotation about the joint rotation axis A2 when the rotational linkage mechanism 20 is rotated in the dynamic loading mode. Referring to FIGS. 5 and 6, the inner ring member 52 comprises a central inner ring plate 60 and proximal and distal inner ring plates 62. The proximal and distal inner ring plates 62 are attached to the central inner ring plate 60 and protrude radially outward of the central inner ring plate. The outer radial surface of the central inner ring plate 60 and the proximal and distal inner ring plates 62, therefore, define a groove 66 that extends circumferentially around the central inner ring plate. The groove 66 broadly functions as a guide for guiding rotation of the outer ring member 50 about the joint rotation axis A2 with respect to the inner ring member 52. The outer ring member 50 defines a radially inwardly extending tongue 68 shaped and arranged for being slidingly received in the groove 66. In the dynamic loading mode, the tongue 68 slides in the groove 66 to guide rotation of the outer ring member 50 about the joint rotation axis A2. Although a tongue and groove mechanism is used guide rotation of the outer ring member relative to the inner ring member in the illustrated embodiment, other embodiments can use other guide mechanisms without departing from the scope of the invention.

Referring to FIGS. 3 and 6, the inner ring member 52 is operatively connected to the wrist and hand splint 26 to rotate conjointly with the wrist and hand splint (see FIGS. 4B and 4D) about the joint rotation axis A2. The rotational linkage mechanism 20 includes a mounting bracket 70 mounted on a radially inner portion of the central inner ring plate 60. The mounting bracket 70 is fixed to the central inner ring plate 60 for conjoint rotation with the inner ring member 52. The mounting bracket 70 is also fixedly secured to the wrist and hand splint 26 for mutual rotation therewith. Thus, as the inner ring member 52 rotates about the joint rotation axis A2, the mounting bracket 70 and splint 26 rotate conjointly therewith. Moreover, when an arm is received in the orthosis 10 and the inner ring member 52 rotates about the joint rotation axis A2, the forearm is either pronated or supinated depending on the direction of rotation P or S. As explained below, when the forearm reaches a maximum range of supination (e.g., as shown in FIGS. 4D and 4E) or pronation (e.g., as shown in FIGS. 4B and 4C), it stops rotating and causes the splint 26, mounting bracket 70 and inner ring member 52 to, likewise, resist further rotation. Further driving of the actuation mechanism 16 in the same direction, therefore, drives rotation of the outer ring member 50 about the inner ring member 52 as the inner ring member is held in place by the fully pronated or supinated forearm.

Figure 7:
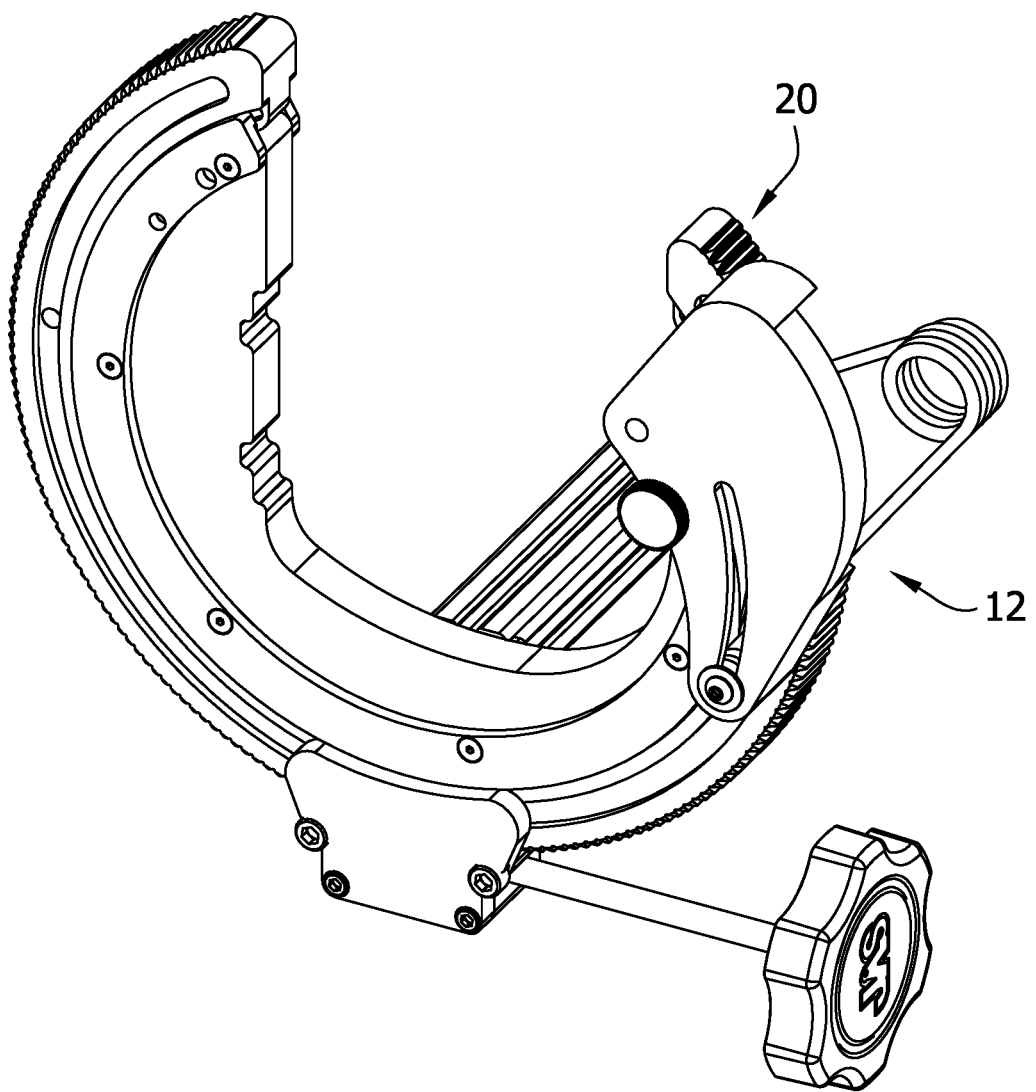
FIG. 7 is a photo of the orthosis illustrating a dynamic force mechanism operating in a static loading mode.
Figure 8:
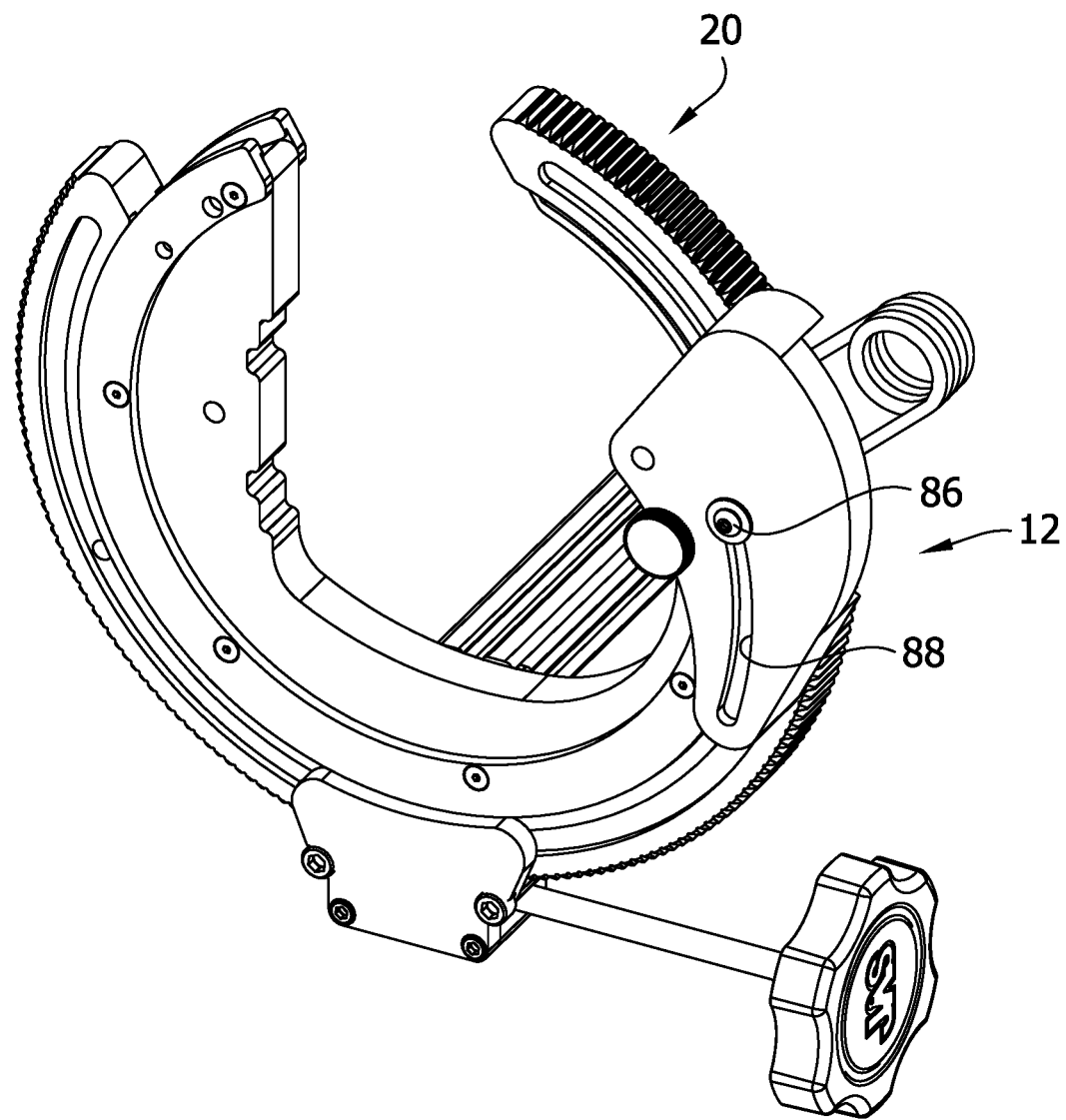
FIG. 8 is a photo of the orthosis illustrating the dynamic force mechanism operating in a dynamic loading mode.
Figure 10A:
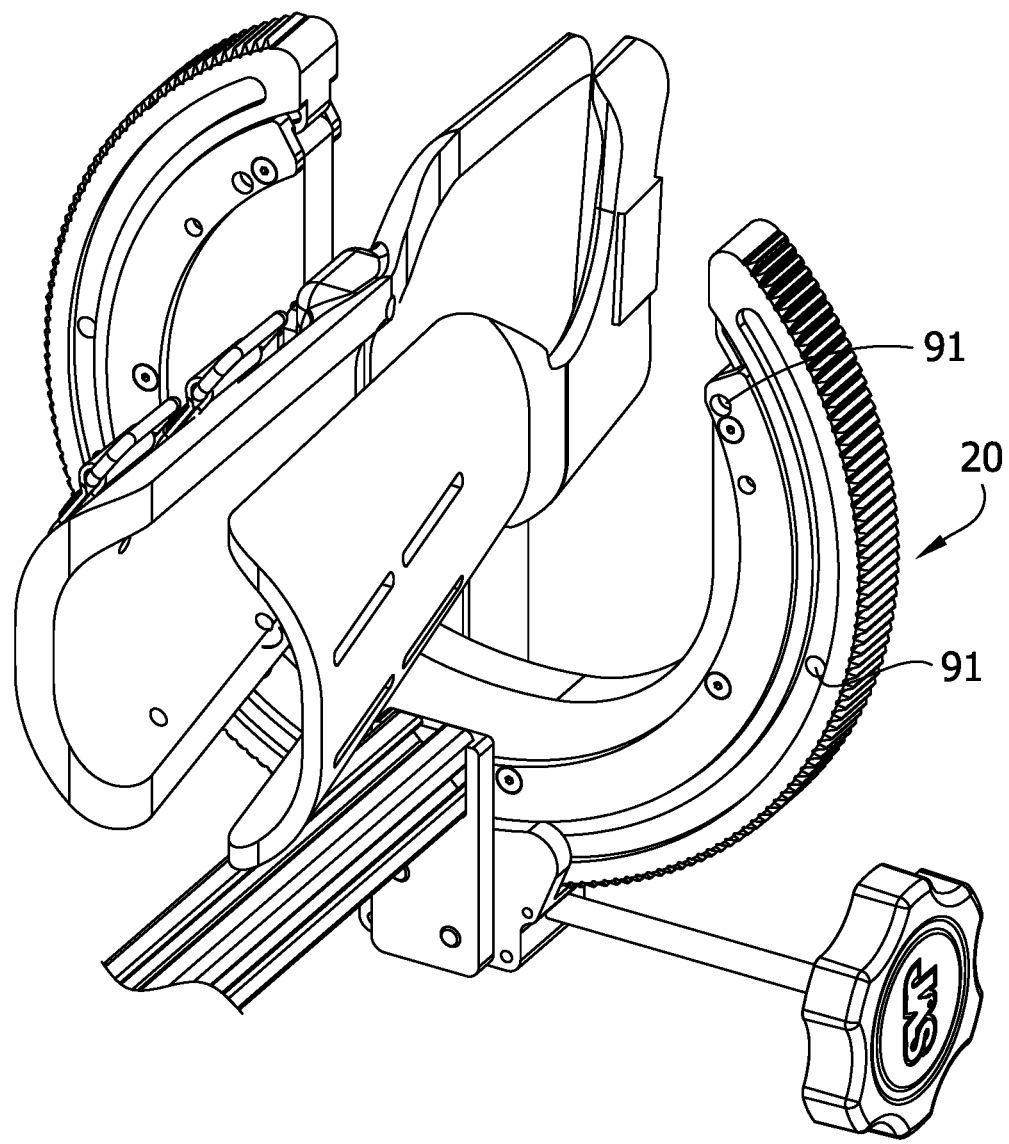
FIG. 10A is a photo of the orthosis with the dynamic force mechanism removed.
Figure 10B:
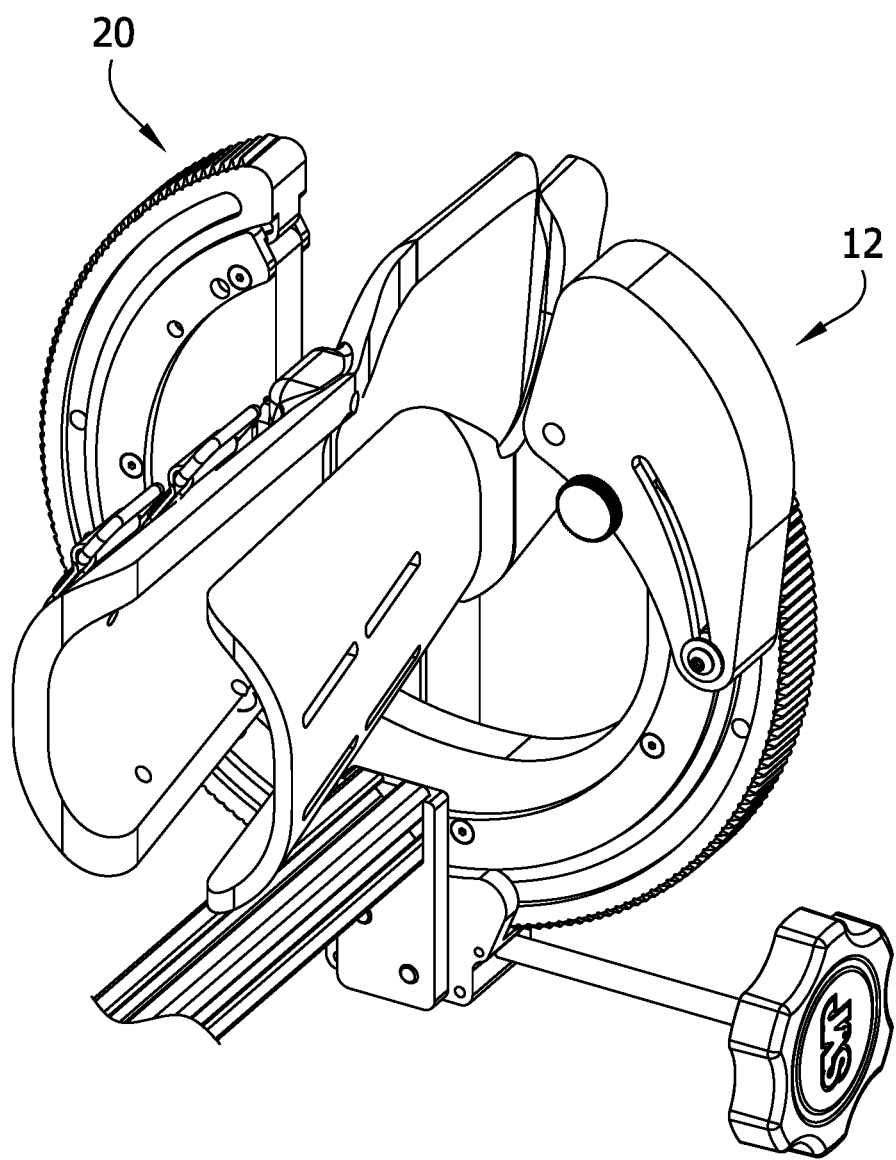
FIG. 10B is a photo similar to FIG. 10A with the dynamic force mechanism installed.
Figure 11A:
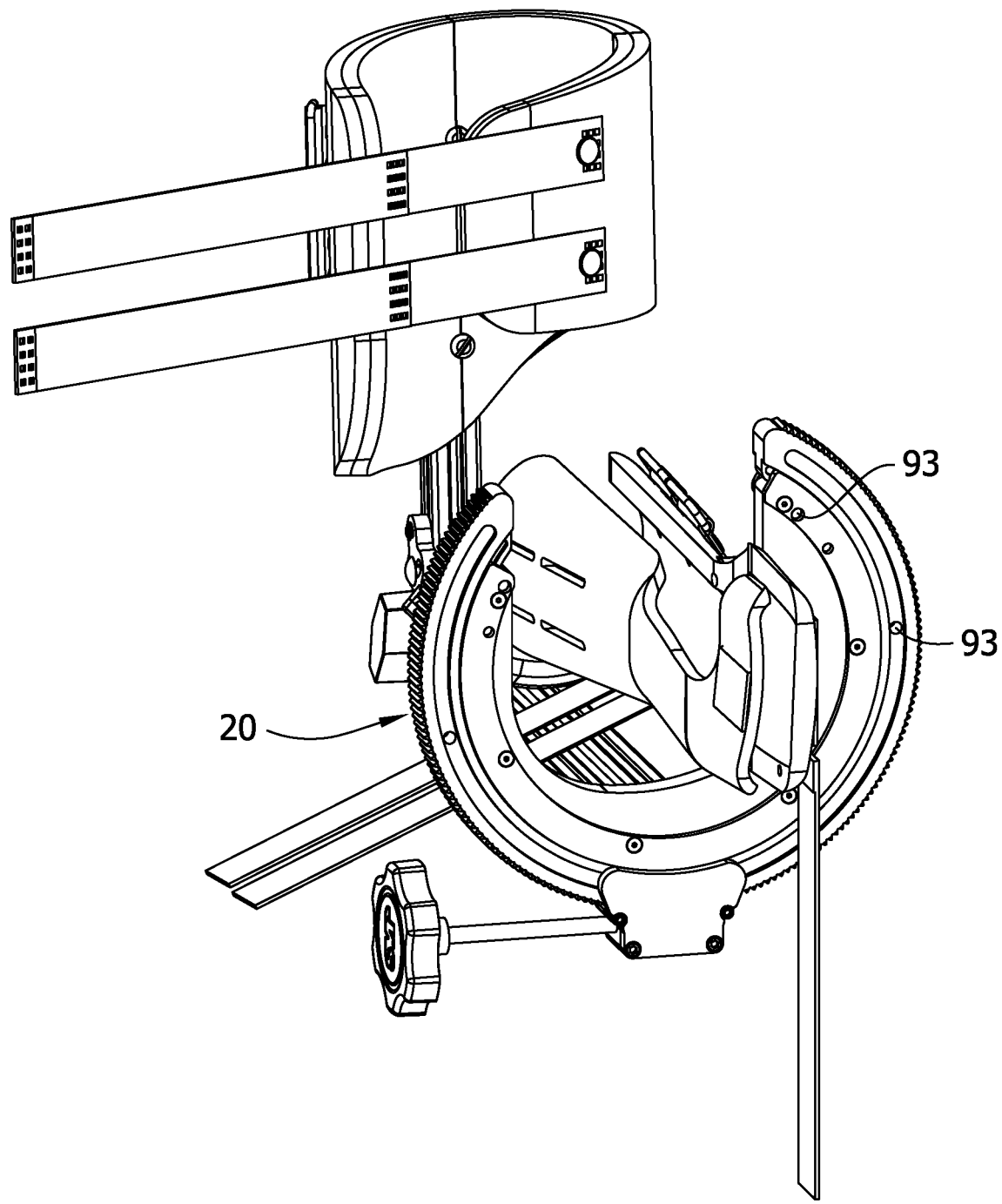
FIG. 11A is another photo of the orthosis with the dynamic force mechanism removed.
Figure 11B:
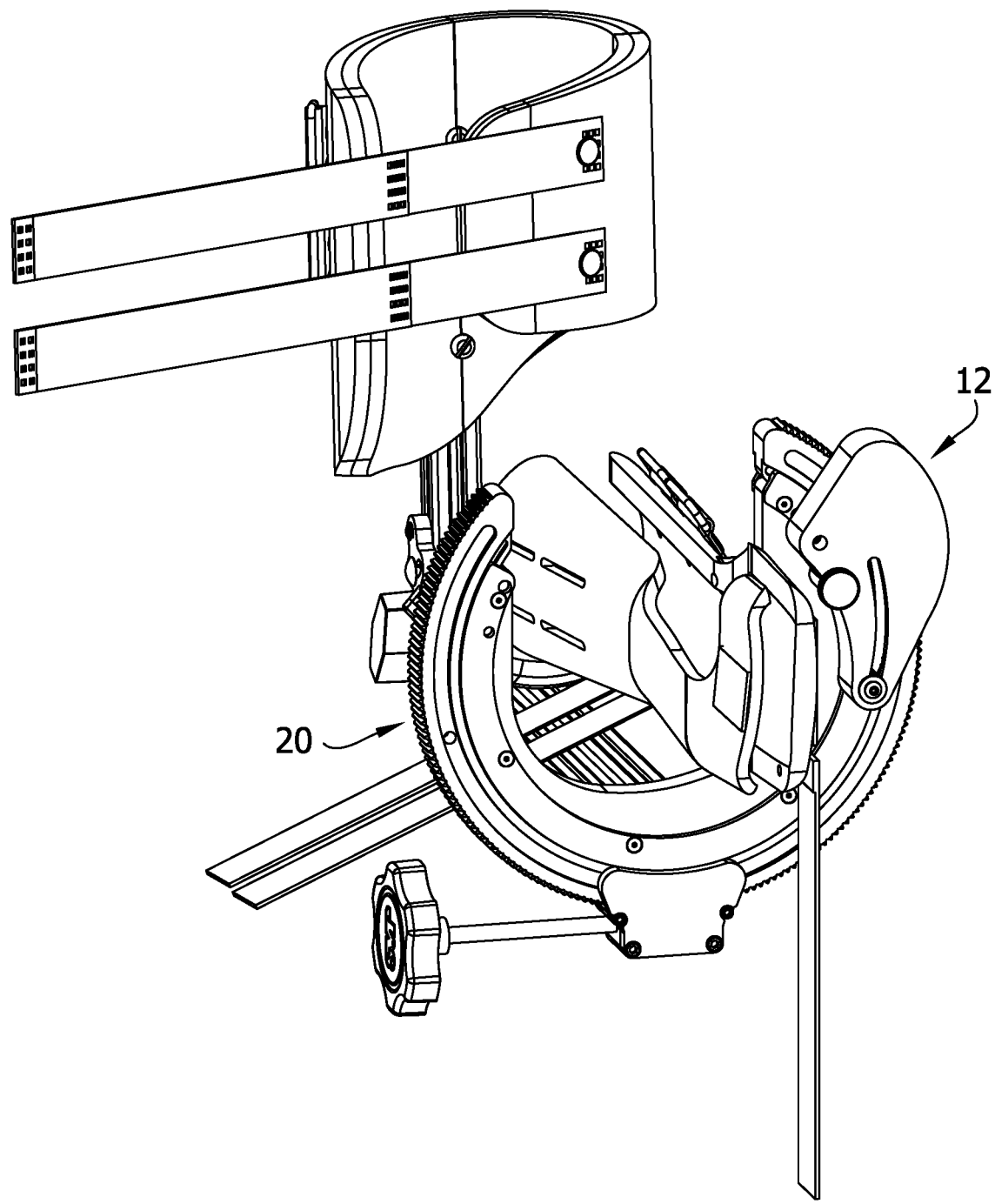
FIG. 11B is a photo similar to FIG. 11A with the dynamic force mechanism installed.

As shown in FIGS. 7 and 8, the dynamic force mechanism 12 is operatively connected to the rotational linkage mechanism 20 to urge the inner ring member 52 toward rotational alignment with the outer ring member 50 after the outer ring member has moved relative to the inner ring member in the dynamic loading mode. In the illustrated embodiment, the dynamic force mechanism 12 is a selectively replaceable cartridge. As shown in FIGS. 10A-10B and 11A-11B the cartridge is selectively installable on the proximal end of the rotational linkage mechanism 20 (FIG. 10B) and the distal end of the rotational linkage mechanism 20 (FIG. 11B). As will be discussed in further detail below, when the cartridge 12 is installed on the proximal end of the rotational linkage mechanism 20, the orthotic 10 is configured to provide dynamic supination of the forearm. And with the cartridge 12 installed on the distal end of the rotational linkage mechanism 20, the orthotic 10 is configured to provide dynamic pronation of the forearm. In other embodiments, the position of the cartridge relative to the rotational linkage could be altered (e.g., reversed, etc.) for pronating and supinating a forearm without departing from the scope of the invention.

Figure 9A:
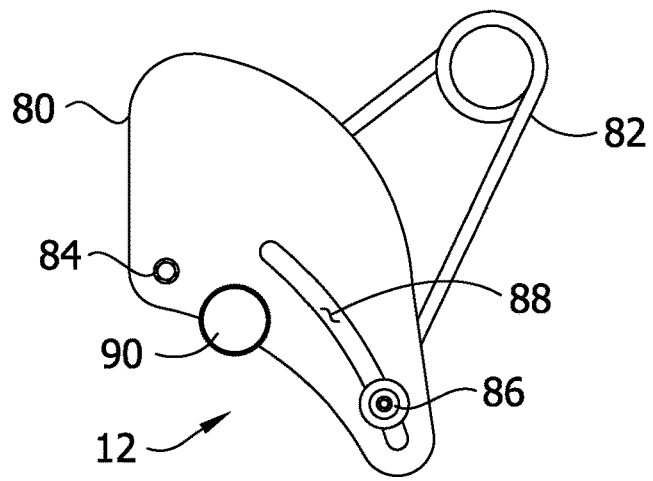
FIGS. 9A-9C are perspectives of the dynamic force mechanism.
Figure 9B:
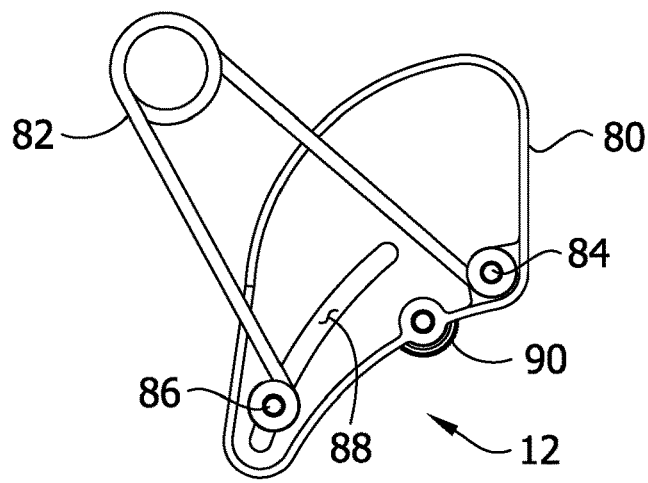

Referring again to FIGS. 9A-9C, the cartridge 12 includes a guide housing 80 that covers a force element 82 configured to impart a rotational force between the outer ring member 50 and the inner ring member 52. In the illustrated embodiment, the force element 82 is a torsion spring, but other suitable force mechanisms can also be used without departing from the scope of the invention. A first pin 84 is attached to the housing 80 and selectively connects one end of the torsion spring 82 to the inner ring member 52. A second pin 86 is slidably received in a guide slot 88 in the housing 80 and selectively connects an opposite end of the torsion spring to the outer ring member 50. As shown in FIG. 10A, the first and second pins are configured to be operatively received in corresponding sockets 91 on the proximal ends of the outer and inner ring members 50, 52 when the cartridge is mounted on the distal end of the rotational linkage mechanism. As shown in FIG. 11A, the sockets first and second pins 84, 86 are configured to be operatively received in corresponding sockets 93 when the cartridge 12 is mounted on the distal end of the rotational linkage mechanism 20. Referring again to FIGS. 9A-9C, a thumb screw 90 or other manually securable fastener can be used to selectively fasten the cartridge 12 to the proximal and distal sides of the housing. When the thumb screw 90 fastens the cartridge 12 to the rotational linkage mechanism 20, the pins 84, 86 mate with the corresponding sockets 91, 93 on the proximal and distal ends of the rotational linkage mechanism 20 to operatively connect the torsion spring 82 to the outer and inner ring members 50, 52.

Figure 9C:
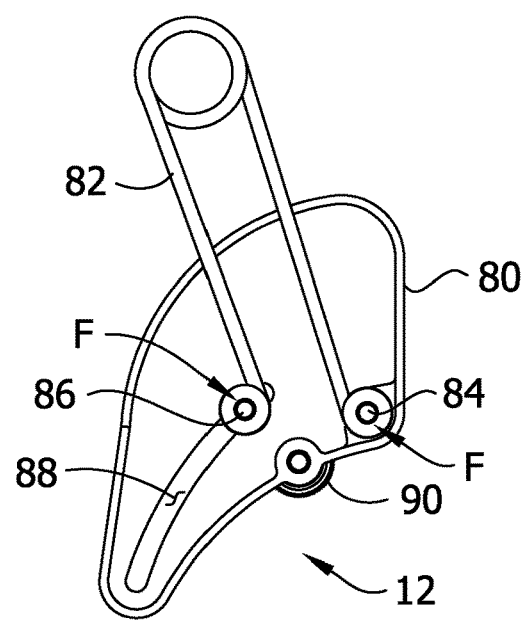

As shown in FIGS. 8 and 9C, when the outer ring member 50 rotates relative to the inner ring member 52 in the dynamic loading mode, the torsion spring 82 compresses. When the outer ring member 50 rotates relative to the inner ring member 52, the pin 86 slides through the guide slot 88 in the housing 80 toward the pin 84. The housing 80 forms a stop that inhibits the second pin 86 from sliding beyond a point associated with a certain configuration of the torsion spring (e.g., where the legs of the torsion spring are oriented about parallel to one another). The relative movement of the first and second pins 84, 86 compresses the torsion spring 82, which imparts a dynamic force F on the first and second pins 84, 86. The force F is transmitted through the pins 84, 86 to the ring members 50, 52 and urges the inner ring member toward rotational alignment with the outer ring member (e.g., in FIG. 4C the force F would urge the inner ring member 52 clockwise toward rotational alignment with the outer ring member 50, in FIG. 4E the force F would urge the inner ring member counterclockwise toward rotational alignment with the outer ring member 50). The outer ring 50 is held in place by the actuation mechanism 16, so the spring forces tend to cause the inner ring 52 member to gradually creep against the reactionary forces of the fully supinated or pronated forearm toward rotational alignment with the outer ring member.

An exemplary method of using the orthosis 10 will now be briefly described. A subject's arm is first mounted in the orthosis 10 so that the upper arm is received in the cuff 24 and the hand and wrist is received in the splint 26. The cuff and splint 24, 26 are tightened to operatively secure the arm in the orthosis 10. Depending on whether the subject's forearm is to be stretched in supination or pronation, the dynamic force cartridge 12 should be installed on either the proximal or distal ends of the rotational linkage mechanism 20. The remainder of this example assumes that the stretching protocol calls for supination of the forearm. Thus, the dynamic force cartridge 12 is installed on the proximal end of the rotational linkage mechanism 20. It will be understood that the protocol could be reversed by installing the dynamic force cartridge 12 on the distal end of the rotational linkage mechanism and rotating the input shaft 34 in the opposite direction.

With the arm properly installed in the orthotic 10 and the cartridge 12 positioned on the proper end of the rotational linkage mechanism 20, the actuation mechanism 16 is actuated to drive the rotational linkage mechanism in the supination direction S in the static loading mode. The knob 36 is rotated to rotate the input shaft 34, which rotates the worm gear 40 about the axis A1. The worm gear 40 rotates the outer ring member 50 about the joint rotation axis A2. The dynamic force cartridge 12 transfers torque from the outer ring member 50 to the inner ring member 52, splint 26, and forearm. And because the forearm provides little resistance to the initial supination (e.g., within the forearm's range of supination motion), the inner ring member 52, splint 26, and forearm rotate conjointly with the outer ring member 50. The knob 36 is rotated further to further drive the rotational linkage mechanism 20 in static loading to stretch the forearm until the forearm reaches its maximum range of motion in the supination direction S.

When the forearm reaches its maximum range of motion in the supination direction S, it resists further rotation in the supination direction. As a result, the forearm imparts a reactionary force in a direction opposite the supination direction S upon the inner ring member 52. As the knob 38 is further rotated, the outer ring member 50 continues to rotation in the supination direction S in the dynamic loading mode. The outer ring member 50 rotates relative to the inner ring member 50, splint 26, and forearm. As the outer ring member 50 rotates relative to the inner ring member 52, the second pin 86 slides with the outer ring member through the guide slot 88. The second pin 86 moves closer to the first pin 84 to compress the torsion spring 82. The compressed spring 82 imparts spring forces F on the first and second pins 84, 86. The spring force F acting against the second pin 86 is insufficient to overcome the holding force of the worm gear 40 against the worm wheel teeth 44 on the outer ring member 50. The spring force F imparted on the first pin 84 transfers through the first pin to the inner ring member 52, and further to the splint 26 and forearm. Slowly, the dynamic force F continually applied on the forearm eventually causes further supination of the forearm, allowing the inner ring member 52 to rotate toward rotational alignment with the inner ring member. By stretching the forearm in the supination direction S beyond its maximum range of motion, the range of motion is extended.

Figure 12:
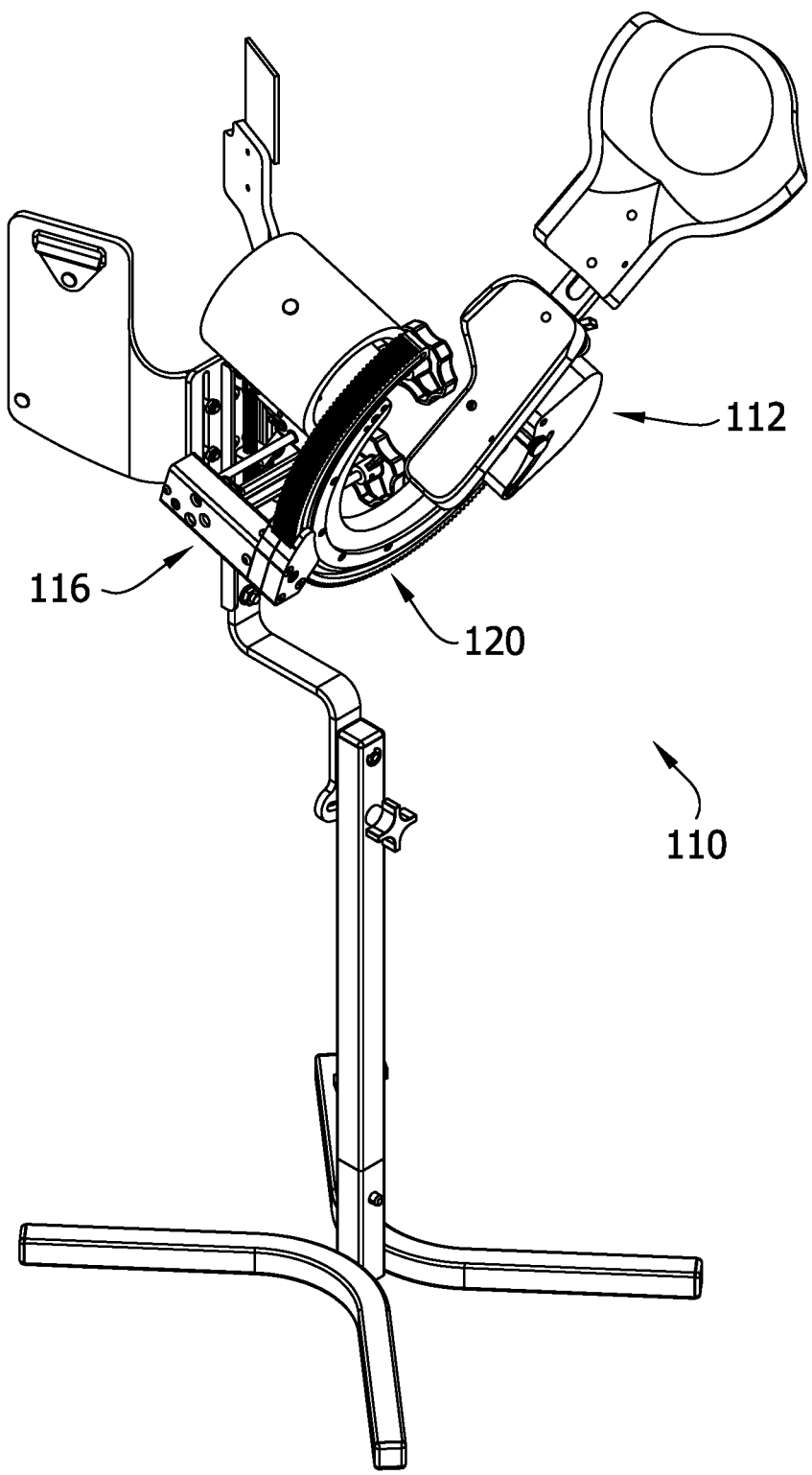
FIG. 12 is perspective of another orthosis.

Referring to FIG. 12, another embodiment of an orthosis is generally indicated at reference number 110. The orthosis 110 can be used like the orthosis 10 as a combination dynamic and static-progressive stretch orthosis. Like the orthosis 10, the orthosis 110 includes a dynamic force mechanism 112, actuation mechanism 116, and rotational linkage mechanism 120. These components function in substantially the same way as the corresponding features of the forearm orthosis 10. But whereas the orthosis 10 is used to stretch a forearm in supination and pronation, the orthosis 110 is used to stretch an upper arm in internal and external rotation.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An orthosis for increasing range of motion of a body joint, the orthosis comprising:
    a rotational linkage mechanism having a driving link and a driven link configured for rotation about a joint axis, the driven link being selectively attachable to a body part to rotate the body part about the joint axis;
    an actuator mechanism operatively connected to the driving link and configured to rotate the driving link; and
    a dynamic force mechanism operatively connected between the driving link and driven link to impart a dynamic force upon the driven link when the driving link rotates relative to the driven link as the driving link is rotated by the actuator mechanism and the driven link resists rotation with the driving link due to a resistance force imparted on the driven link by the body part reaching a maximum range of motion, the dynamic force being transferred through the driven link to the body part;
    wherein the driving link and driven link each define a gap for receiving a portion of the body part.

2. The orthosis as set forth in claim 1, wherein the dynamic force mechanism is selectively installable on the orthosis in a first position in which the dynamic force mechanism is configured to transmit the dynamic force in a first direction and a second position in which the dynamic force mechanism is configured to transmit the dynamic force in a second direction opposite the first direction.

3. The orthosis as set forth in claim 1, wherein the dynamic force mechanism comprises a selectively removable cartridge.

4. The orthosis as set forth in claim 1, wherein the driving link and the driven link are configured to rotate together until the driven link resists rotation with the driving link due to the resistance force imparted on the driven link by the body part.

5. The orthosis as set forth in claim 1, wherein the dynamic force mechanism is coupled to the driving link and the driven link.

6. The orthosis as set forth in claim 1, wherein the dynamic force mechanism includes a force element configured to impart the dynamic force on the driven link.

7. The orthosis as set forth in claim 6, wherein the force element is a spring.

8. The orthosis as set forth in claim 1, wherein the dynamic force mechanism includes a stop to limit the amount of rotation of the driving link relative to the driven link.

9. The orthosis as set forth in claim 1, further comprising a cuff coupled to the driven link, the cuff configured to be selectively attachable to the body part to selectively attach the driven link to the body part.

10. The orthosis as set forth in claim 1, wherein the actuator mechanism includes a drive assembly operatively connected to the driving link and configured to drive rotation of the driving link.

11. The orthosis as set forth in claim 10, wherein the actuator mechanism includes a transmission assembly operatively connected between the drive assembly and the driving link.

12. The orthosis as set forth in claim 10, wherein the drive assembly includes a knob configured to be manually rotated to drive rotation of the driving link.

13. The orthosis as set forth in claim 1, wherein the driving link is a generally annular member and the driven link is a generally annular member.

14. The orthosis as set forth in claim 13, wherein the driving link and the driven link are concentric relative to one another.

15. The orthosis as set forth in claim 14, wherein the driven link is directly coupled to the driving link.

16. The orthosis as set forth in claim 15, wherein the driven link and driving link are slidably coupled to one another such that the driving link slides relative to the driven link when the driving link rotates relative to the driven link.

17. The orthosis as set forth in claim 16, wherein driving link includes a tongue slidably received in a groove of the driven link to slidably couple the driven link and driving link to one another.

18. The orthosis as set forth in claim 1, wherein the driving link includes a plurality of teeth, wherein the actuator mechanism includes a gear meshed with the plurality of teeth of the driving link so that rotation of the gear drives rotation of the driving link.

19. The orthosis as set forth in claim 1, wherein the dynamic force mechanism drives rotation of the driven link.

* * * * *